US00PP18679P2

(12) United States Plant Patent
Vandenberg

(10) Patent No.: US PP18,679 P2
(45) Date of Patent: Apr. 1, 2008

(54) ***CHRYSANTHEMUM* PLANT NAMED 'DEEP WISH'**

(50) Latin Name: *Chrysanthemum×morifolium*
Varietal Denomination: Deep Wish

(75) Inventor: Cornelis P. Vandenberg, Fort Myers, FL (US)

(73) Assignee: Yoder Brothers, Inc., Barberton, OH (US)

( * ) Notice: Subject to any disclaimer, the term of this patent is extended or adjusted under 35 U.S.C. 154(b) by 0 days.

(21) Appl. No.: 11/637,849

(22) Filed: Dec. 12, 2006

(51) Int. Cl.
*A01H 5/00* (2006.01)

(52) U.S. Cl. ..... Plt./287
(58) Field of Classification Search ..... Plt./287
See application file for complete search history.

*Primary Examiner*—Kent Bell
(74) *Attorney, Agent, or Firm*—C. A. Whealy

(57) ABSTRACT

A new and distinct cultivar of *Chrysanthemum* plant named 'Deep Wish', characterized by its upright plant habit; dark green-colored foliage; freely and uniformly flowering habit; decorative-type inflorescences; attractive purple-colored ray florets; response time about 68 days; strong peduncles; and good postproduction longevity.

1 Drawing Sheet

Botanical designation: *Chrysanthemum×morifolium.*
Cultivar denomination: 'Deep Wish'.

BACKGROUND OF THE INVENTION

The present invention relates to a new and distinct cultivar of *Chrysanthemum* plant, botanically known as *Chrysanthemum×morifolium,* commercially grown as a cut flower and hereinafter referred to by the name 'Deep Wish'.

The new *Chrysanthemum* is a product of a planned breeding program conducted by the Inventor in Alva, Fla. The objective of the program is to create and develop new cut *Chrysanthemum* cultivars having inflorescences with desirable floret coloration and good inflorescence form and substance.

The new *Chrysanthemum* is a naturally-occurring whole plant mutation of the *Chrysanthemum×morifolium* cultivar Wish, disclosed in U.S. Plant Pat. No. 12,873. The new *Chrysanthemum* was discovered and selected by the Inventor as a single flowering plant within a population of plants of the cultivar Wish in March, 2000, in Alva, Fla. The selection of this plant was based on its desirable inflorescence color and good form and substance.

Asexual reproduction of the new *Chrysanthemum* by terminal cuttings in a controlled environment in Alva, Fla. since May, 2000, has shown that the unique features of this new *Chrysanthemum* are stable and reproduced true to type in successive generations.

SUMMARY OF THE INVENTION

Plants of the cultivar Deep Wish have not been observed under all possible environmental conditions. The phenotype may vary somewhat with variations in environment such as temperature, daylength and light intensity, without, however, any variance in genotype.

The following traits have been repeatedly observed and are determined to be the unique characteristics of 'Deep Wish'. These characteristics in combination distinguish 'Deep Wish' as a new and distinct cultivar of *Chrysanthemum:*

1. Upright plant habit.
2. Dark green-colored foliage.
3. Freely and uniformly flowering habit.
4. Decorative-type inflorescences that are about 8 cm in diameter.
5. Attractive purple-colored ray florets.
6. Response time about 68 days.
7. Strong peduncles.
8. Good postproduction longevity with inflorescences and foliage maintaining good substance and color for about three weeks in an interior environment.

Plants of the new *Chrysanthemum* differ from plants of the parent, the cultivar Wish, in the following characteristics:

1. Plants of the new *Chrysanthemum* flower later than plants of the cultivar Wish.
2. Plants of the new *Chrysanthemum* and the cultivar Wish differ in ray floret color as plants of the cultivar Wish have dark pink-colored ray floret.

Plants of the new *Chrysanthemum* can be compared to plants of the *Chrysanthemum* cultivar Royalist, disclosed in U.S. Plant Pat. No. 9,076. In side-by-side comparisons conducted in Alva, Fla., plants of the new *Chrysanthemum* differed from plants of the cultivar Royalist in the following characteristics:

1. Plants of the new *Chrysanthemum* were shorter than plants of the cultivar Royalist.
2. Plants of the new *Chrysanthemum* had darker green-colored leaves than plants of the cultivar Royalist.
3. Plants of the new *Chrysanthemum* had darker colored ray florets than plants of the cultivar Royalist.

BRIEF DESCRIPTION OF THE PHOTOGRAPHS

The accompanying photographs illustrate the overall appearance of the new *Chrysanthemum.* These photographs show the colors as true as it is reasonably possible to obtain in colored reproductions of this type. Colors in the photographs may differ slightly from the color values cited in the detailed botanical description which accurately describe the colors of the new *Chrysanthemum*.

The photograph at the top of the sheet comprises a side perspective view of a typical flowering stem of 'Deep Wish'.

The photograph at the bottom of the sheet comprises a close-up view of typical inflorescences of 'Deep Wish'.

DETAILED BOTANICAL DESCRIPTION

In the following description, color references are made to The Royal Horticultural Society Colour Chart, 1995 Edition, except where general terms of ordinary dictionary significance are used. The aforementioned photographs and following observations and measurements describe plants grown in Bogota, Colombia during the summer in a polyethylene-covered greenhouse and under conditions and practices which approximate those generally used in commercial *Chrysanthemum* production. During the production of the cut flowers, day temperatures ranged from 20° C., to 25° C. night temperatures ranged from 4° C. to 9° C. and light levels ranged from 3,000 to 4,000 foot-candles. Measurements and numerical values represent averages for typical flowering plants. The photographs and measurements were taken when plants were about two months old from planting.

Botanical classification: *Chrysanthemum×morifolium* cultivar Deep Wish.

Parentage: Naturally-occurring whole plant mutation of the *Chrysanthemum×morifolium* cultivar Wish, disclosed in U.S. Plant Pat. No. 12,873.

Propagation:

*Type.*—Terminal vegetative cuttings.

*Time to initiate roots.*—About ten to 14 days with soil temperatures of about 18° C. to 21° C.

*Root description.*—Fine, fibrous; white in color.

*Rooting habit.*—Freely branching.

Plant description:

*Appearance.*—Herbaceous decorative-type cut flower.

*Flowering stem description.*—Aspect: Erect. Length: About 87 cm. Spray diameter: About 15 cm. Stem diameter: About 6.5 mm. Internode length: About 3.5 cm. Texture: Pubescent; longitudinally ridged. Color: 147B.

*Foliage description.*—Arrangement: Alternate; simple. Length: About 10.4 cm. Width: About 5.1 cm. Apex: Acuminate. Base: Attenuate. Margin: Palmately lobed; irregularly serrate; sinuses parallel to slightly divergent. Texture, upper and lower surfaces: Pubescent; veins prominent on lower surface, Color: Developing foliage, upper and lower surfaces: 147A. Fully expanded foliage, upper surface: 147A; venation, 147C. Fully expanded foliage, lower surface: 147B; venation, 147C. Petiole: Length: About 1.4 cm. Diameter: About 4 mm. Texture, upper and lower surfaces: Pubescent. Color, upper surface: 147B. Color, lower surface: 147C.

Inflorescence description:

*Appearance.*—Decorative-type inflorescence form with elongated oblong to quilled-shaped ray florets. Inflorescences borne on terminals, arising from leaf axils. Ray and disc florets develop acropetally on a capitulum. Uniform flowering habit.

*Fragrance.*—Faint; spicy.

*Flowering response.*—Under natural conditions, plant flower in the autumn/winter in the Northern Hemisphere. At other times of the year, inflorescence initiation and development can be induced under short day/long night conditions (at least 13.5 hours of darkness). Plants exposed to two weeks of long day/short night conditions after planting followed by photoinductive short day/long night conditions flower about 68 days later.

*Postproduction longevity.*—In an interior environment, inflorescences and foliage will maintain good color and substance for about three weeks in an interior environment.

*Quantity of inflorescences.*—Freely flowering habit, about seven inflorescences per stem develop.

*Inflorescence size.*—Diameter: About 8 cm. Depth (height): About 2.7 cm. Disc diameter: About 2 mm. Receptacle diameter: About 2.6 cm. Receptacle height: About 7 mm.

*Inflorescence buds.*—Shape: Oblate. Height: About 1.8 cm. Diameter: About 1.8 cm. Color: 75C to 75D.

*Ray florets.*—Shape: Elongated oblong to ligulate or quilled. Surface: Concave. Aspect: Initially incurved; with development, roughly perpendicular to the pedicel. Length: About 3.8 cm. Width: About 1 cm. Apex: Emarginate. Base: Fused. Texture: Smooth, glabrous; velvety; longitudinally ridged. Number of ray florets per inflorescence: About 350 arranged in about 20 whorls. Color: When opening, upper surface: 77C. When opening, lower surface: 75C. Fully opened, upper surface: 78B; color becoming closer to 78D with development. Fully opened, lower surface: 78C.

*Disc florets.*—Shape: Tubular, elongated. Length: About 4 mm. Diameter: About 1 mm. Number of disc florets per inflorescence: About eight; inconspicuous. Color: Apex: Close to 4B. Mid-section: Close to 4D. Base: Close to 157A.

*Phyllaries.*—Quantity per inflorescence/arrangement: About 32 arranged in about four whorls. Length: About 1 cm. Width: About 3 mm. Shape: Elliptic. Apex: Acute. Base: Truncate. Margin: Entire. Texture, upper surface: Smooth, glabrous. Texture, lower surface: Pubescent. Color, upper surface: Close to 146A. Color, lower surface: Close to 147A.

*Peduncles.*—Length: About 18.7 cm. Diameter: About 2 mm. Angle: About 30° to 40° from vertical. Strength: Strong. Texture: Pubescent; longitudinally ridged. Color: Close to 148A.

*Reproductive organs.*—Androecium: None observed. Gynoecium: Pistil length: About 6 mm. Stigma shape: Bi-parted. Stigma color: Close to 13A. Style length: About 4 mm. Style color: Close to 145D. Ovary color: Close to 157A.

*Seed/fruit.*—Seed and fruit production has not been observed.

Disease/pest resistance: Resistance to pathogens and pests common to *Chrysanthemums* has not been observed on plants grown under commercial conditions.

Temperature tolerance: Plants of the new *Chrysanthemum* have demonstrated good tolerance to low temperatures of about 4° C. and high temperatures of about 35° C.

It is claimed:

1. A new and distinct *Chrysanthemum* plant named 'Deep Wish' as illustrated and described.

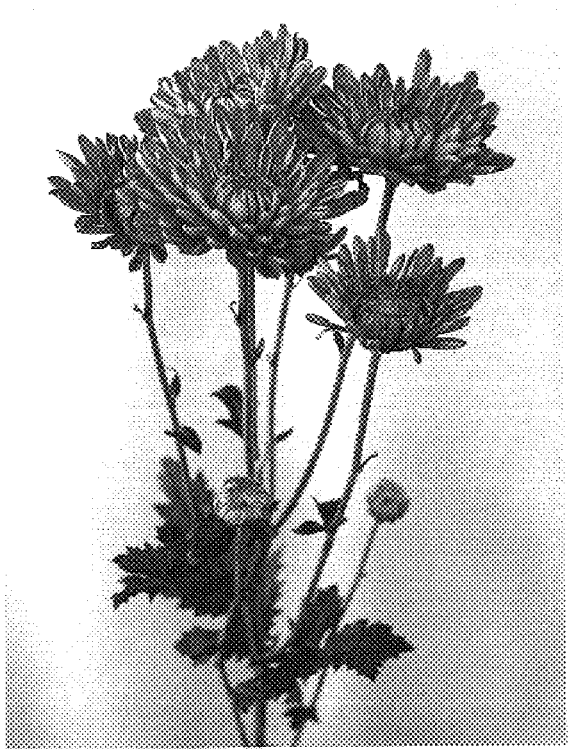
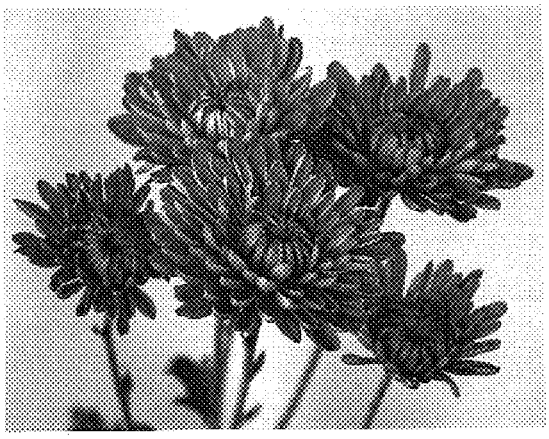

* * * * *